United States Patent
Ferguson et al.

(10) Patent No.: US 7,211,225 B2
(45) Date of Patent: May 1, 2007

(54) FILTER DEVICES FOR DEPOSITING MATERIAL AND DENSITY GRADIENTS OF MATERIAL FROM SAMPLE SUSPENSION

(75) Inventors: Gary William Ferguson, Burnaby (CA); Marija Us-Krasovec, Ljubljana (SI); Margareta Flezar, Ljubljana (SI); Mario Zganec, Golnik (SI); Jaka Lavrencak, Ljubljana (SI); Branko M. Palcic, Vancouver (CA)

(73) Assignee: Perceptronix Medical Inc., Vancouver, BC (CA)

( * ) Notice: Subject to any disclaimer, the term of this patent is extended or adjusted under 35 U.S.C. 154(b) by 453 days.

(21) Appl. No.: 10/228,353

(22) Filed: Aug. 26, 2002

(65) Prior Publication Data

US 2004/0038425 A1 Feb. 26, 2004

(51) Int. Cl.
*G01N 30/00* (2006.01)
(52) U.S. Cl. .................. 422/101; 422/100; 422/102; 422/68.1; 436/177; 436/178
(58) Field of Classification Search ............... 422/58, 422/99, 100, 101, 102, 68.1
See application file for complete search history.

(56) References Cited

U.S. PATENT DOCUMENTS

| | | |
|---|---|---|
| 4,250,830 A | 2/1981 | Leif |
| 4,391,710 A | 7/1983 | Gordon |
| 4,395,493 A | 7/1983 | Zahniser |
| 4,614,109 A | 9/1986 | Hofmann |
| 4,961,432 A | 10/1990 | Guirguis |
| 5,301,685 A | 4/1994 | Guirguis |
| 5,419,279 A | 5/1995 | Carrico |
| 5,480,484 A | 1/1996 | Kelley |
| 5,503,802 A | 4/1996 | Polk, Jr. et al. |
| 5,626,751 A * | 5/1997 | Kikuchi et al. ........ 210/321.75 |
| 5,674,395 A | 10/1997 | Stankowski et al. |
| 5,679,154 A | 10/1997 | Kelley |
| 5,784,193 A | 7/1998 | Ferguson |
| 5,889,881 A | 3/1999 | MacAulay |
| 5,970,782 A | 10/1999 | Hartley et al. |
| 5,976,824 A | 11/1999 | Gordon |
| 6,010,909 A | 1/2000 | Lapidus |
| 6,026,174 A | 2/2000 | Palcic |

(Continued)

FOREIGN PATENT DOCUMENTS

JP 08266837 10/1996

*Primary Examiner*—Jill Warden
*Assistant Examiner*—Samuel P. Siefke
(74) *Attorney, Agent, or Firm*—Trexler, Bushnell, Giangiorgi, Blackstone & Marr, Ltd.

(57) ABSTRACT

The present invention provides a simple, inexpensive apparatus for and method of capturing biological or other material from sample suspensions on a collection surface and for depositing captured material on a receiving surface, such as a microscope slide, for observation and analysis. Accordingly, cytological material may be deposited in near monolayers for the detection of disease. In one embodiment of the present invention, density gradients of material are captured and deposited, thus providing a desired range of concentrations for examination. In another embodiment multiple depositions or multiple slides may be made from the same sample suspension. The method and apparatus to exploit this new method are both presented for various applications. The dimensions of material captured and deposited may be controlled and used in conjunction with microscope slides that confine material to specific regions of interest.

3 Claims, 10 Drawing Sheets

U.S. PATENT DOCUMENTS

| | | |
|---|---|---|
| 6,162,401 A | 12/2000 | Callaghan |
| 6,225,125 B1 | 5/2001 | Lapidus |
| 6,309,362 B1 | 10/2001 | Guirguis |
| 6,316,189 B1 | 11/2001 | Haddad |
| 6,358,474 B1 | 3/2002 | Dobler |
| 6,742,659 B2 * | 6/2004 | Clark et al. .................. 210/474 |
| 2001/0012493 A1 * | 8/2001 | Zermani ...................... 422/101 |

* cited by examiner

FILTER DEVICES FOR DEPOSITING MATERIAL AND DENSITY GRADIENTS OF MATERIAL FROM SAMPLE SUSPENSION

BACKGROUND OF THE INVENTION

The present invention relates to the capture of cells or other material from a sample suspension and the deposition of cells or other material onto an appropriate receiving surface, such as a microscope slide for observation.

In the field of cytology, human and machine vision systems perform effectively on near mono-layer depositions of cellular material. Expanded use of machine vision for slide examination, a growing number of special stains and the development of molecular markers have increased the need to prepare multiple representative depositions or multiple slides from the same sample suspension. However, care must be taken in the deposition of cellular material used for cytological examination. In particular, to diagnose disease, slides must be representative of the sample suspension, which ideally is representative of the patient. And if multiple cellular depositions are made on the same or on different slides, then each of these depositions must also be representative of the sample suspension. Achieving an appropriate concentration and distribution of material for examination or analysis is a limitation of many sample preparation techniques. Therefore an intent of the present invention is to overcome some of these limitations.

Three common techniques used to deposit cells from a sample suspension onto microscope slides are: centrifugation, filter transfer and fluid evaporation. Examples of centrifugation are taught in U.S. Pat. No. 4,391,710 to Gordon entitled "*Cytocentrifuge*", U.S. Pat. No. 5,679,154 to Kelley et al. entitled "Cytology centrifuge apparatus ", U.S. Pat. No. 5,480,484 to Kelley et al. entitled "Cytology centrifuge apparatus", U.S. Pat. No. 6,162,401 to Callaghan, entitled "Cytofunnel arrangement", and U.S. Pat. No. 5,419,279 to Carrico, Jr. et al. entitled "Apparatus for depositing and staining cytological material on a microscope slide".

Filter transfer is taught in U.S. Pat. No. 4,395,493 to Zahniser and U.S. Pat. No. 5,976,824 to Gordon entitled "Method and apparatus for collecting a cell sample from a liquid specimen". And an example of fluid evaporation is taught in U.S. Pat. No. 5,784,193 to Ferguson entitled "Microscope slide with removable layer and method".

Variations of these methods are taught in U.S. Pat. No. 5,419,279 to Carrico, Jr. et al. entitled "Apparatus for depositing and staining cytological material on a microscope slide", U.S. Pat. No. 6,225,125 to Lapidus, entitled "Method and apparatus for controlled instrumentation of particles with a filter device", U.S. Pat. No. 6,309,362 to Guirguis entitled "Method and apparatus for automatically separating particulate matter from a fluid", and U.S. Pat. No. 6,358,474 to Dobler et al. entitled "Device and Method for Isolating Cell Material Out of a Tissue Medium and/or a Liquid".

For filter transfer, cellular or other material is collected, typically on a circular filter, and is transferred to the microscope slide by contact, back-pressure or a combination of contact and back-pressure. Other examples of cell deposition onto membrane filters in the prior art are taught by FIG. 4 of U.S. Pat. No. 5,419,279 to Carrico Jr. et al.; FIG. 11 in U.S. Pat. No. 5,679,154 to Kelley et al.; FIG. 2 of U.S. Pat. No. 4,250,830 to Leif; FIG. 3 in U.S. Pat. No. 6,162,401 to Callaghan; and FIG. 5 of U.S. Pat. No. 6,309,362 to Guirguis.

U.S. Pat. No. 6,162,401 to Callaghan teaches cell capture on a filter or membrane in which the filter dimensions are smaller than that of a microscope slide. This prior art does not teach or derive advantage by capturing material on a filter which extends beyond the dimensions of the receiving surface. While capturing material on filters, filter dimensions are typically kept to a minimum since filter deformation may cause inconsistencies in flow and thus material capture by the filter. Under less favorable conditions the filter itself could tear, otherwise fail or its characteristics may be compromised. Similarly, although filters are often supplied in a support structure, when material distribution is important for analysis, flow impediments in the vicinity of the carrier or support structure are viewed as problematic. Therefore, filter dimensions are generally kept to a minimum. Typically, the filter area is smaller and fits entirely within the dimensions of the receiving surface. An example of a departure from this in the prior art is U.S. Pat. No. 5,784,193 to Ferguson, which maintains its advantages and exploits situations when material dimensions exceed that of the exposed region of the slide or receiving surface.

Currently, in cytology, if multiple slides are required from a sample suspension, either the sample is split prior to deposition, or multiple portions (sub-samples) are captured on individual filters, and these are then deposited onto one or more slides for analysis. Multiple depositions are taught in: U.S. Pat. No. 4,250,830 to Leif entitled "*Swinging buckets*", U.S. Pat. No. 4,961,432 to Guirguis, entitled "Modular fluid sample preparation assembly", and U.S. Pat. No. 5,784,193 to Ferguson, entitled "Microscope slide with removable layer and method". The latter reference is of particular interest since it teaches: precise confinement of material to region(s) of interest; protecting the slide from contamination during bulk processing; and independent staining of various regions on the same slide. Products manufactured under this patent include high-tech surface coatings of PVC type materials that are easily removed, resistant to abrasion, and stable during cell fixation and staining. Such coatings as applied in fluid or vapor state are referred to as evaporation methods (see Ferguson column 6, lines 24–29). Additionally, Ferguson specifically teaches the limitations placed on the examination of cellular material when cells are deposited near the edge of the coverslip or microscope slide.

One limitation of using multiple small filters to capture multiple portions of material is that flow rate and other conditions for cell capture must be monitored closely to prevent non-representative samples or inadequate preparations. A non-representative sample, for example, may lack cancerous cells from which to make a diagnosis. Similarly, excess material, sparseness or substantial variations in cellular concentration may impede or otherwise confound diagnosis.

Some of these filter limitations are taught in U.S. Pat. No. 4,395,493 to Zahniser entitled "*Monolayer device using filter techniques*", wherein the capture of cellular material on a filter tape is monitored by a cell counter. U.S. Pat. No. 4,614,109 to Hoffman teaches membrane testing by measuring differential pressure across it. U.S. Pat. No. 6,010,909 to Lapidus and U.S. Pat. No. 6,225,125 to Lapidus teach blocking pores. As material is captured, membrane pores are blocked, thus the differential pressure across the membrane provides an estimate of material concentration collected on the filter prior to deposition on a receiving surface. These techniques are designed to ensure that the appropriate concentration of material is captured on each filter. In order to achieve the appropriate concentration of material, however, these techniques are sometimes complicated and require expensive equipment and a substantial amount of time to perform.

Although the concentration of the collected material can be monitored, one difficulty with using multiple filters results not from the design of the device for monitoring the concentration, but from the nature of biological samples. Even in homogeneous samples, various sized clumps of cells, mucus, debris, particulate matter and various contaminants may be present. Therefore, that material which is captured on one small filter may be substantially different than the material captured on a subsequent filter. For a relatively large deposition of material, a few cell clumps or inadequate areas are not uncommon and may or may not impede diagnosis. The probability of capturing non-representative material is related to the surface area of the filter on which the material is collected.

A related difficulty is that once any material is removed from the sample suspension, the characteristics of the sample have changed and replicates are no longer possible. Unfortunately, with filter transfer methods, as cells are captured on the membrane, the concentration of constituents in the sample suspension are altered and therefore subsequent preparations from this sample suspension may no longer be representative. And in some cases, once any material has been removed from the original sample suspension, additional preparations from this may not even be suitable for the intended use. Similarly, repeated blots from the same area of a filter will not produce representative slides.

Another limitation for many analysis techniques, including cytology, is that to be effective, the concentration of material must fall within a target range. Still other test protocols require a target range of specific sample constituents. These target ranges are used to exploit malignancy-associated changes, for example which require predominantly DNA stained, non-overlapping nuclei. Typically, preparations for exploiting malignancy-associated changes include scrapings, aspirates, and washings for the detection of cancer and other diseases. Some of these applications are taught in U.S. Pat. No. 5,889,881 to MacAulay et al. and U.S. Pat. No. 6,026,174 to Palcic et al.

While most cytology-based tests simply require representative samples containing abnormal cells, malignancy-associated changes are measured on ostensibly normal cells. Unfortunately, in the majority of cases the concentration of cells and constituents, in any given sample, is not known a priori. While cell counters, sample dilutions, differential pressure and other techniques are commonly employed to monitor or otherwise control the concentration of cells deposited, these require additional equipment, time and expertise. Even then for a variety of reasons the resulting cell deposition may be inadequate. It is therefore a goal of the present invention to improve the probability that an area adequate for analysis will be deposited on the receiving surface.

The need exists for a rapid, simple, cell deposition method to prepare multiple representative slides from a sample suspension. In addition, a more restricted set of applications would benefit from a cell or material deposition in the form of a concentration gradient.

SUMMARY OF THE INVENTION

A general object of the present invention is to provide a means for capturing one or more depositions from a sample suspension, which is representative of the sample suspension.

Another general object of the present invention is to provide a filter from which one or more depositions which are representative of a sample suspension can be made, simply.

Another object of the present invention is to provide a filter from which a concentration gradient can be made which is representative of a sample suspension.

Another object of the present invention is to provide a filter from which several deposits can be made in a time-efficient manner.

Another object of the present invention is provide a filter from which a concentration gradient can be made without the need to prepare multiple dilutions of the sample suspension.

Another object of the present invention to provide a filter from which a concentration gradient can be captured and deposited in a time-efficient manner.

Another object of the present invention is to provide a filter which provides the ability to make several deposits from the material collected by the filter in which all of the deposits are representative of the sample suspension from which the material was collected.

Briefly, and in accordance with the foregoing, the present invention provides a simple and inexpensive apparatus for and method of depositing material from a sample suspension. Accordingly, cells or material may be deposited in near mono-layers for the detection of disease. The apparatus and method of the present invention collects material from a single sample suspension. The collected material is then used to make multiple deposits on a single slide or on multiple slides. A filter assembly of the present invention also provides for the collection and deposit of concentration gradients. Thus, providing a desired range of cell concentrations for cytological examination and ensuring that an appropriate concentration of material is present on the receiving surface for the desired analysis.

The present invention provides a method and apparatus which overcome some of the limitations presented in the prior art and which provides additional advantages over the prior art. Such advantages will become clear upon a reading of the attached specification in combination with a study of the drawings.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE ILLUSTRATED EMBODIMENTS

Figure 1:
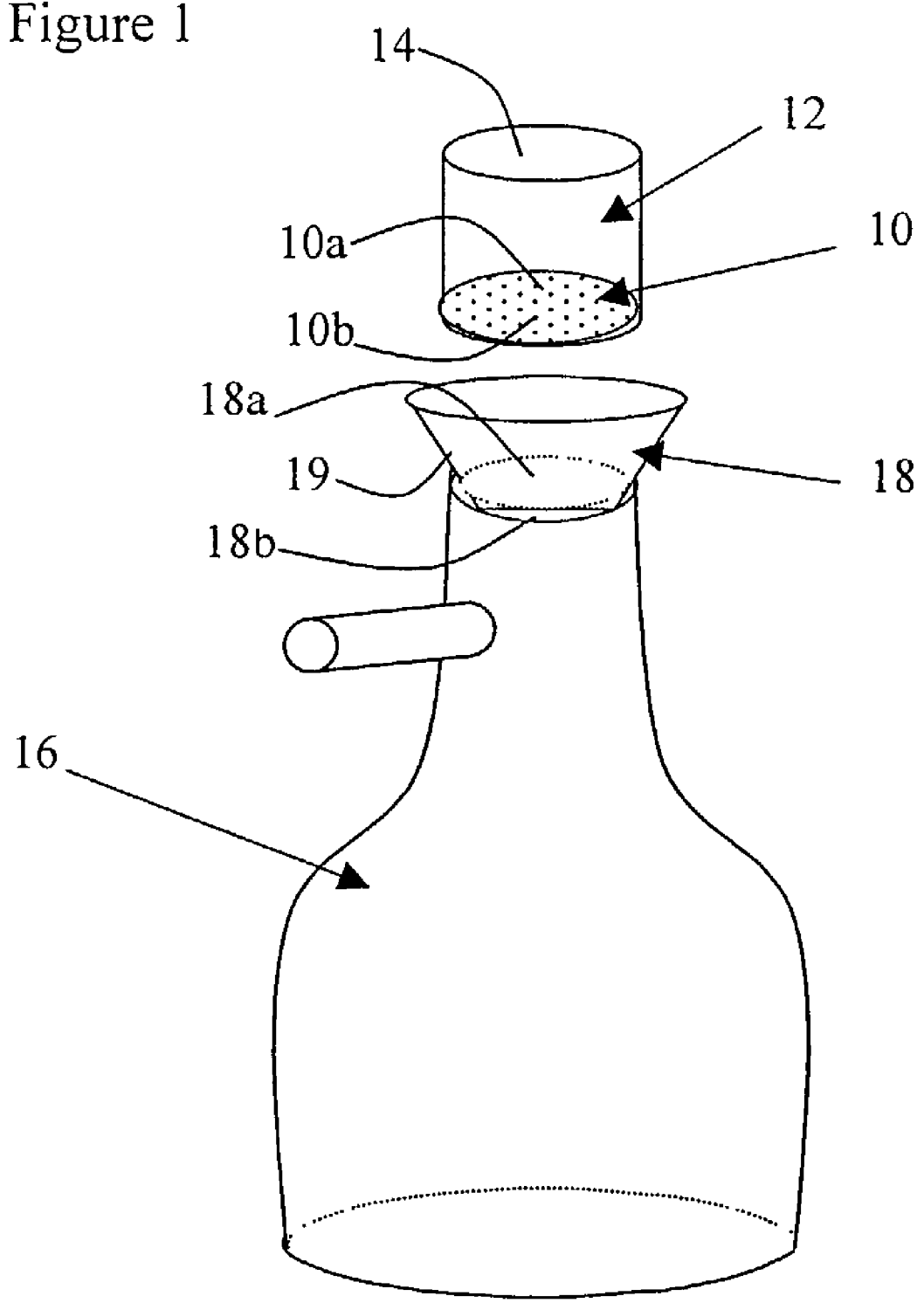
FIG. 1 is a partially exploded view of a vacuum and filter assembly including a filter in accordance with an embodiment of the invention; in connection with an apparatus used to deposit material onto the filter.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

FIG. 1 shows a generally disk-shaped filter 10 installed at the bottom of a sample chamber 12. The filter 10 has an upper collection surface 10a and a lower surface 10b. The sample chamber 12 is generally cylindrical, providing a top opening 14 for the introduction of a sample suspension. The perimeter of the filter 10 is slightly smaller than the interior dimension of the sample chamber 12. Thus the perimeter of the filter 10 extends to the interior surface of the sample chamber 12. The sample chamber 12 is placed over a vacuum assembly 16 and is preferably fitted thereto through an adapter cone 18. The adaptor cone 18 includes a circular upper opening 18a and a smaller circular lower opening 18b. A tapered wall 19 extends between the upper opening 18a and the lower opening 18b. The tapered wall of the adaptor cone 18 is capable of accommodating various-sized sample chambers and various sized vacuum assemblies.

In use, the adaptor cone 18 is placed within an opening at the top of the vacuum assembly 16. The sample chamber 12 is then placed within the adaptor cone 18 and sample suspension is introduced to the sample chamber 12 through the opening 14. The sample suspension begins to flow through the filter 10 and the vacuum assembly 16 is used to assist in drawing the sample suspension through the filter 10. Alternatively, positive pressure could be applied to the sample chamber 12 to facilitate the passage of the sample through the filter 10. Any one of a number of known methods can be used to assist passage of sample suspension through the filter 10. For example, a syringe (not shown) can be used to apply force to the sample suspension to draw or push the sample suspension through the filter 10. Alternatively, the force of gravity alone can be used to draw sample suspension through the filter 10.

As the sample suspension is drawn through the filter 10, material to be examined is captured on the top surface 10a of the filter 10. The filter 10 along with the cells or other material captured by the filter 10 is then removed from the sample chamber 12. Since approximately the same volume of sample suspension flows through each unit area of the filter 10, a relatively uniform distribution of material will be captured on the filter surface 10a. In cytology, capturing and transferring a uniform distribution of material to the slide, in a near-monolayer for examination, is typically the desired intent.

Figure 2:
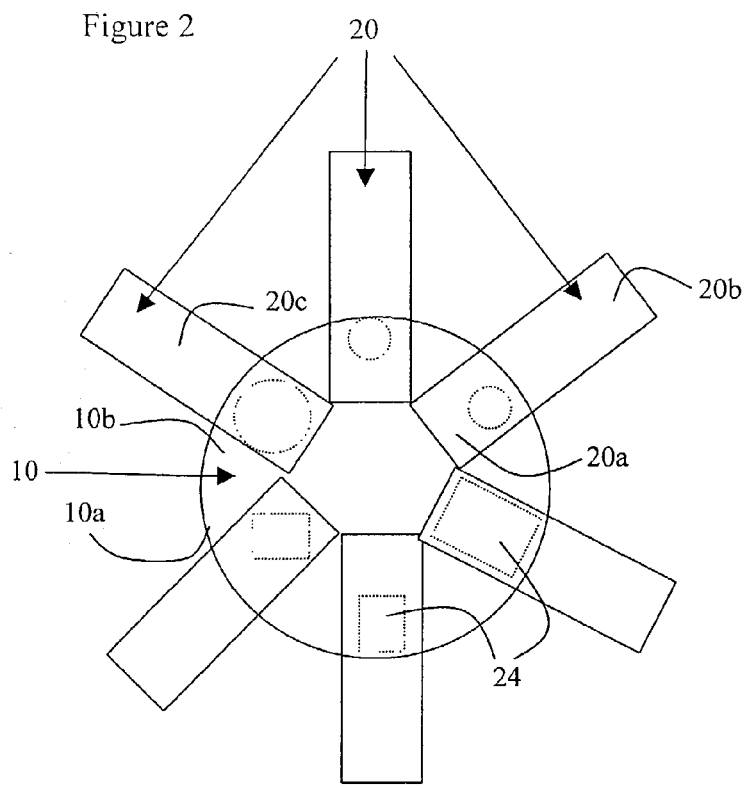
FIG. 2 is a top view of the filter of FIG. 1 positioned over a multitude of slides on which material collected by the filter is to be placed.

As shown in FIG. 2, each microscope slide 20 has a first end 20a, a second end 20b, and a receiving surface 20c. In the arrangement shown, six microscope slides are positioned such that the respective receiving surface 20c, of each slide 20, faces upward and the first end 20a of each slide is positioned near a central point, thus allowing the filter 10 to be positioned over the slides. While it is not essential that the filter be positioned over the receiving surfaces 20c of all the slides 20, simultaneously, as a matter of convenience in preparing multiple slides, and to help ensure that a fresh area of filter is used for each deposition, such a configuration is preferred.

Figure 2A:
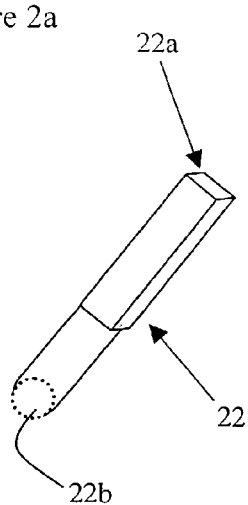
FIG. 2a is a perspective view of a blotter which is used to transfer material collected by the filter onto a microscope slide or appropriate receiving surface.

FIG. 2a shows a blotter 22, preferably made of rubber or firm sponge. An advantage of using a firm sponge is that it may be soaked in fixative if required or desired, as described in U.S. Pat. No. 4,395,493. A rubber blotter is satisfactory when the use of a fixative is not necessary.

The blotter 22 has a first contact end 22a which is rectangular in cross-section and a second contact end 22b which is circular in cross-section. The blotter 22 will be used to assist the deposit of material on the slides 20 as will be described herein.

To deposit material from filter 10 to the slides 20, the user positions and presses the blotter 22 against side 10b of the filter 10, thus causing filter surface 10a, with captured material, to be pressed against the receiving surface 20c of the slide, thus transferring cells or material to the receiving surface 20c, creating a deposit area 24 on the slide 20. In this manner the deposit area 24 will contain a near mono-layer deposit of material that approximates the shape and dimensions of the contacting surface of the blotter 22. Cells or material on the slide 20 may be further processed, stained or otherwise treated prior to examination.

Although six slides are shown in FIG. 2, any convenient configuration for multiple slides may be used. In addition, the number of deposits made from the filter 10 is limited by the area of the filter, in that an unused or fresh portion of the filter should be used to create each deposit. Alternatively, rather than placing a single deposit on each slide, it may be desirable to make more than one deposit on the receiving surface 20c of a single slide. Because portions of the sample suspension were not removed to create each slide, each of the six slides shown in FIG. 2a contains a cell or material deposit which is representative of the sample suspension.

Figure 3:
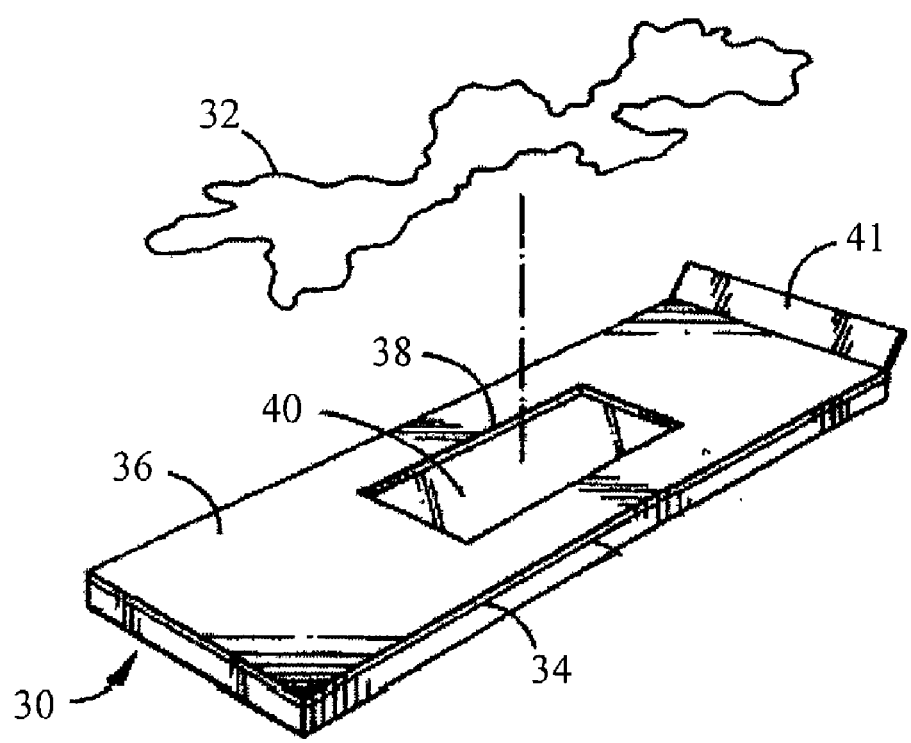
FIG. 3 is a perspective view of a prior art removable layer microscope slide.

The filter 10 can be used in conjunction with a variety of different receiving surfaces and slides. For example, the filter 10 can be used in conjunction with a removable layer slide such as that shown in FIG. 3. Such a slide is described in U.S. Pat. No. 5,784,193, providing a means to confine material deposited on the slide to a particular region. The removable layer 30 comprises a mounting surface 34 with a removable surface layer 36 applied to the mounting surface 34. Removable layer 36 is formed with an opening 38 to define an exposed region 40 on the mounting surface 34 for retaining material 32 to be observed. A tab 41 is provided to facilitate removal of the surface layer 36, which when removed, leaves deposited material confined within to exposed region 40.

Figure 4A:
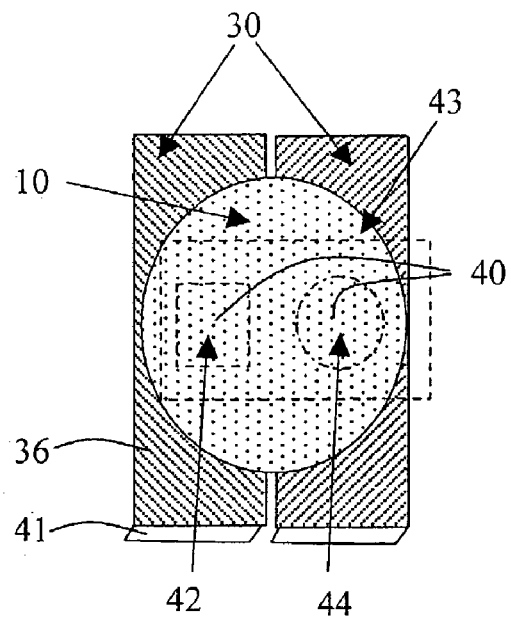
FIG. 4a is a top view of two removable layer microscope slides, shown in connection with the filter of FIG. 1.
Figure 4B:
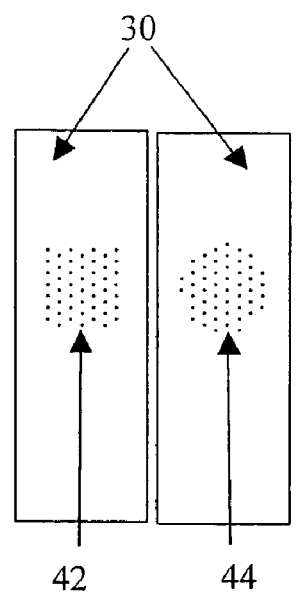
FIG. 4b is a top view of the removable layer microscope slides of FIG. 4a with material deposited and the removable layer, removed.

The filter 10 of the present invention can also be used to prepare multiple slides that exploit the advantages of removable surface layer slides as shown in FIGS. 4a and 4b. As shown in FIG. 4a, the filter 10 substantially covers the exposed regions 40 of two slides positioned adjacent one another. Two exposed regions 40 by way of example are indicated by rectangular region 42 and circular region 44. As described above, a blotter can be used to assist in the transfer of cells or material from the filter 10 to the exposed region 40 of each of the slides 30 to regions 42 and 44. As described in U.S. Pat. No. 5,784,193, the surface layer may be removed by lifting tab 41. Such removal may be performed immediately following deposition, between treatment steps, or subsequent to any material processing, if required, or desired. By way of example, a relatively large rectangular blotter with contact area 43 is used to facilitate deposition. Accordingly, after removal of the slide's surface layer, the resulting deposition is shown in FIG. 4b with cells or material confined within region 42 and 44.

Figures 5, 5A:
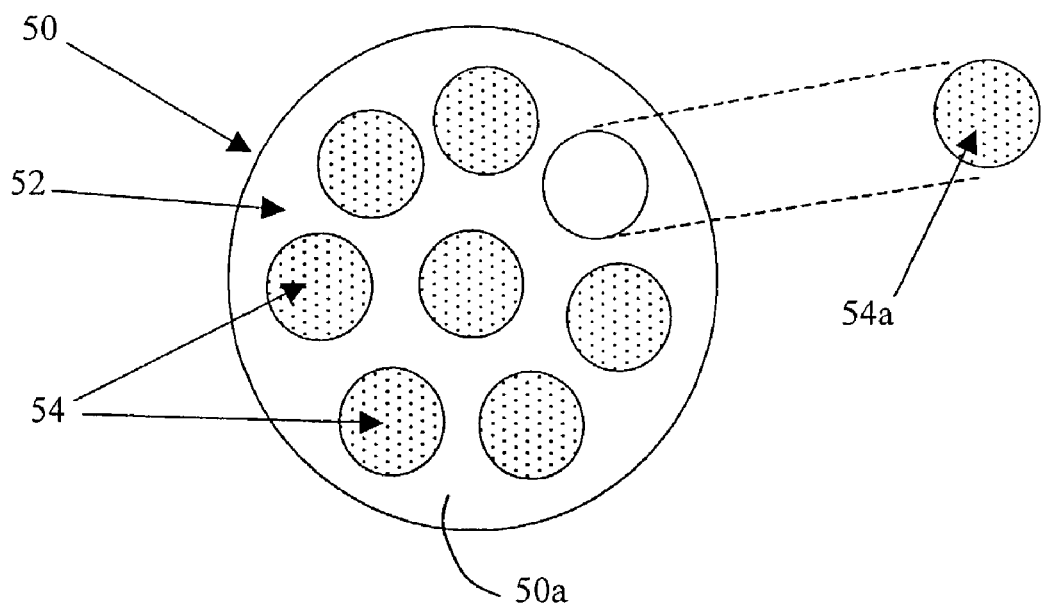
FIG. 5 is a top view of another embodiment of the present invention.
FIG. 5a shows another aspect of the embodiment represented in FIG. 5

Another embodiment of the present invention is shown in FIG. 5. The filter 50 is generally disk shaped and includes a collection surface 50a and a bottom surface (not shown). The filter 50 also includes non-porous area 52 and several porous areas 54. The porous areas 54 are circular and are spaced within the non-porous area 52. Perforation may be provided around each of the porous areas 54 to facilitate removal of the porous areas 54 from the non-porous areas 52 as will be described herein. (Any type of perforation, striation, indentation, or other means to facilitate removal of the porous areas 54 from the non-porous areas 52 may be used so long as such means do not create a fluid pathway or hamper the strength of characteristics of the collection surface. Some amount of fluid pathway would be acceptable, however, so long as the rate of passage of sample suspension through the pathway is less than or equal to the rate of passage through an identically-sized area of the collection surface.)

As with the embodiment shown in FIGS. 1 and 2, the filter 50 is placed at the bottom of a sample chamber. Sample suspension is introduced into the sample chamber and passes through the porous areas 54 of filter 50. The filter 50 is then removed from the sample chamber and if perforation has been provided around the porous areas 54, pressure is applied to the perforated portions to separate a porous portion 54a from the remainder of the filter 50 as shown in FIG. 5a. The porous portion 54a is then placed over a microscope slide or other receiving surface so that the material collected by the porous portion 54a can be deposited onto the slide. A blotter can also be used to facilitate the transfer of cells or material from the porous portion 54a of the filter 50 to the slide.

If perforations have not been provided around the porous portion 54a may be cut from the non-porous area 52. Alternatively, the entire filter 50 can be inverted as described above with respect to the filter 10 and the porous areas 54 of the filter 50 can be positioned over slides, and deposits can be created by pressing the blotter against the bottom surface of the filter 50 at the location of the porous areas 54. By providing porous areas 54 the size of the deposit area to be created can be controlled independently of the size of the blotter and the user can control more precisely the amount of material to be deposited on the slides.

By such a method, material may be deposited on separate slides or several depositions may be made on the same slide. As with the embodiment previously described, each of these deposits will be representative of the sample suspension. Because only one collection is made from the sample suspension, each of the deposits is representative and the problem with removal of material (sub-sampling) from the sample suspension solution is eliminated. In practice, cytologists use physical or chemical means to assist in the disaggregation of cell clumps and dissolve mucus so as to minimize existing limitation by rendering the sample suspension, homogeneous. While this reduces the problem, it does not eliminate it.

Figure 6A:
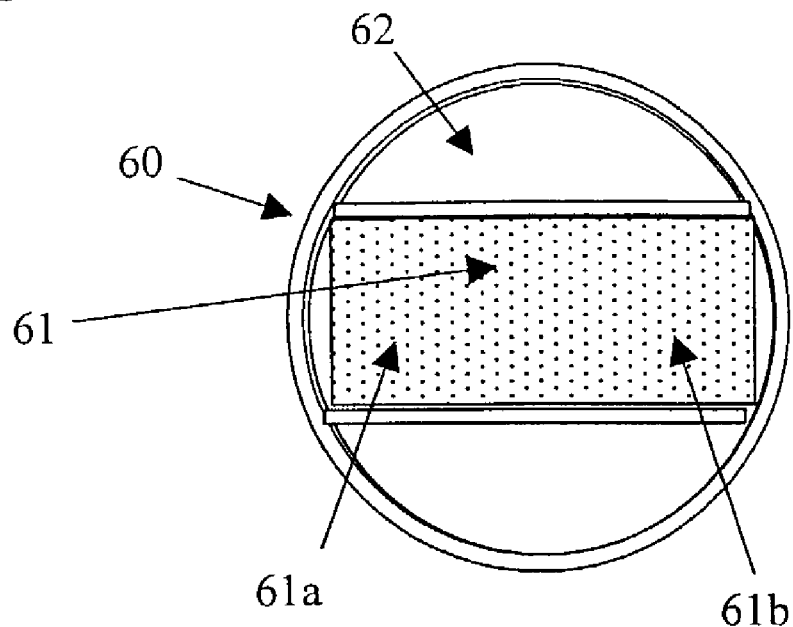
FIG. 6a is a top view of another embodiment of the present invention with a filter mounted within a support structure.
Figure 6B:
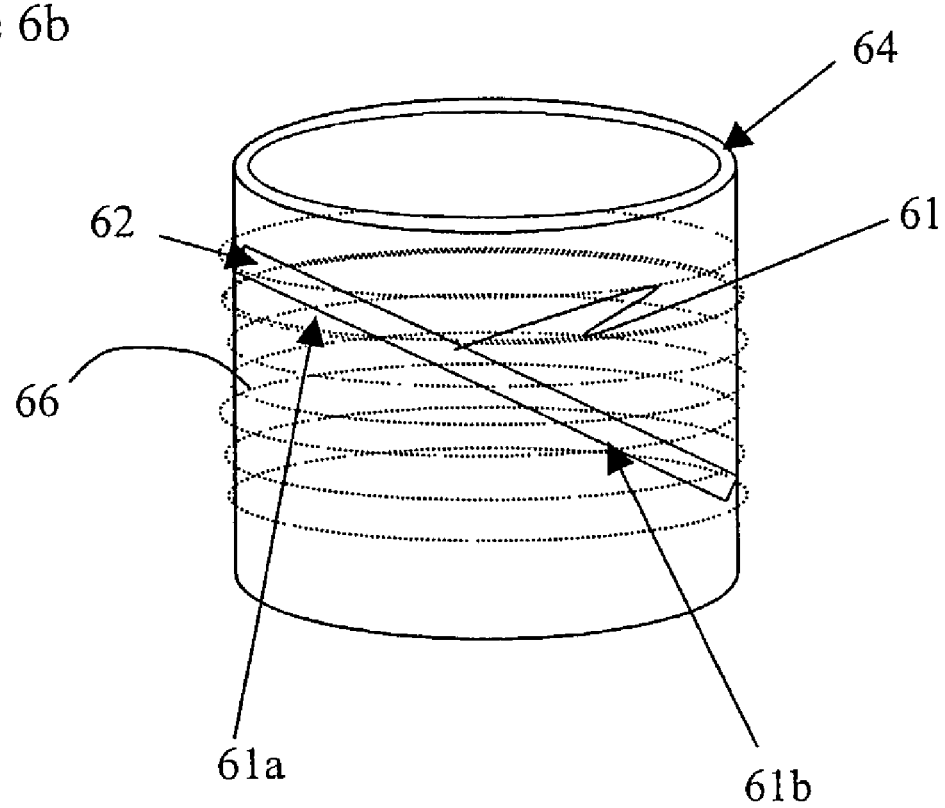
FIG. 6b is a front view of the filter and filter support structure shown in FIG. 6a assembled in a sample chamber.

The present invention can also be used to collect cells from a sample suspension in a manner which allows for analysis of a concentration gradient of material as shown in FIGS. 6a and 6b. The filter assembly 60 includes a filter 61 and a support structure 62 and is positioned within a sample chamber 64. The filter 61 is generally rectangular in shape and has a first end 61a and a second end 61b. The filter 61 is mounted to a circularly-shaped support structure 62. The support structure 62 is non-porous and includes an aperture over which the filter 61 is mounted. The support structure 62 may also include protrusions (not shown) which extend radially outwardly from the perimeter of the support structure for positioning the filter assembly 60 within the sample chamber 64 as will be described herein.

The sample chamber 64 is generally cylindrical and is preferably made of a material with elastic properties such as rubber. Multiple circular striations 66 are spaced along the interior surface of the sample chamber 64. When the filter assembly 60 is mounted within a sample chamber 64, the striations 66 in connection with protrusions extending from the support structure 62 allow the filter assembly 60 to be positioned at a desired angle within the sample chamber 64 as shown in FIG. 6b. The angular orientation of the filter assembly 60 facilitates the capture of a desired density gradient of material. When the filter assembly 60 is positioned within the sample chamber 64, a fluid tight seal is created between the support structure 62 and the sample chamber 64, which causes fluid to flow through the filter 61 rather than around the support structure 62.

Use of the filter assembly 60 begins by determining which striations 66 are to be used to achieve a desired angle at which the filter assembly 60 will be positioned within the sample chamber 64. Using a striation nearer the upper end of the sample chamber 64, the filter assembly 60 is positioned within the sample chamber 64 so that the first end 61a of the filter is positioned proximate the top end of the sample chamber 64 and a second end 61b of the filter is positioned proximate the bottom end of the sample chamber 64. Protrusions extending radially outward from the support structure 62 may be provided to engage the striations 66 on the interior surface of the sample chamber 64.

Sample suspension is introduced into the sample chamber 64 and material passes over the collection surface of the filter assembly 60 and is captured on the filter 61. It may be desirable to wet the surface of the filter 61 and insert the fluid sample into the sample chamber 64 prior to applying any vacuum. Due to the angle of the filter 61, a smaller volume of fluid will pass through the first end 61a of the filter 60 than will pass through the second end 61b of the filter 60. Because the volume of fluid which flows through the filter 61 varies, the quantity of cells or material captured on the filter 61 will also vary. Therefore, a greater concentration of cells or material will be found near the second end 61*b* of the filter 61 than near the first end 61*a* of the filter 61. The varying concentration of cells over the filter 61 represents a concentration gradient of material that is useful for analysis.

Figure 6C:
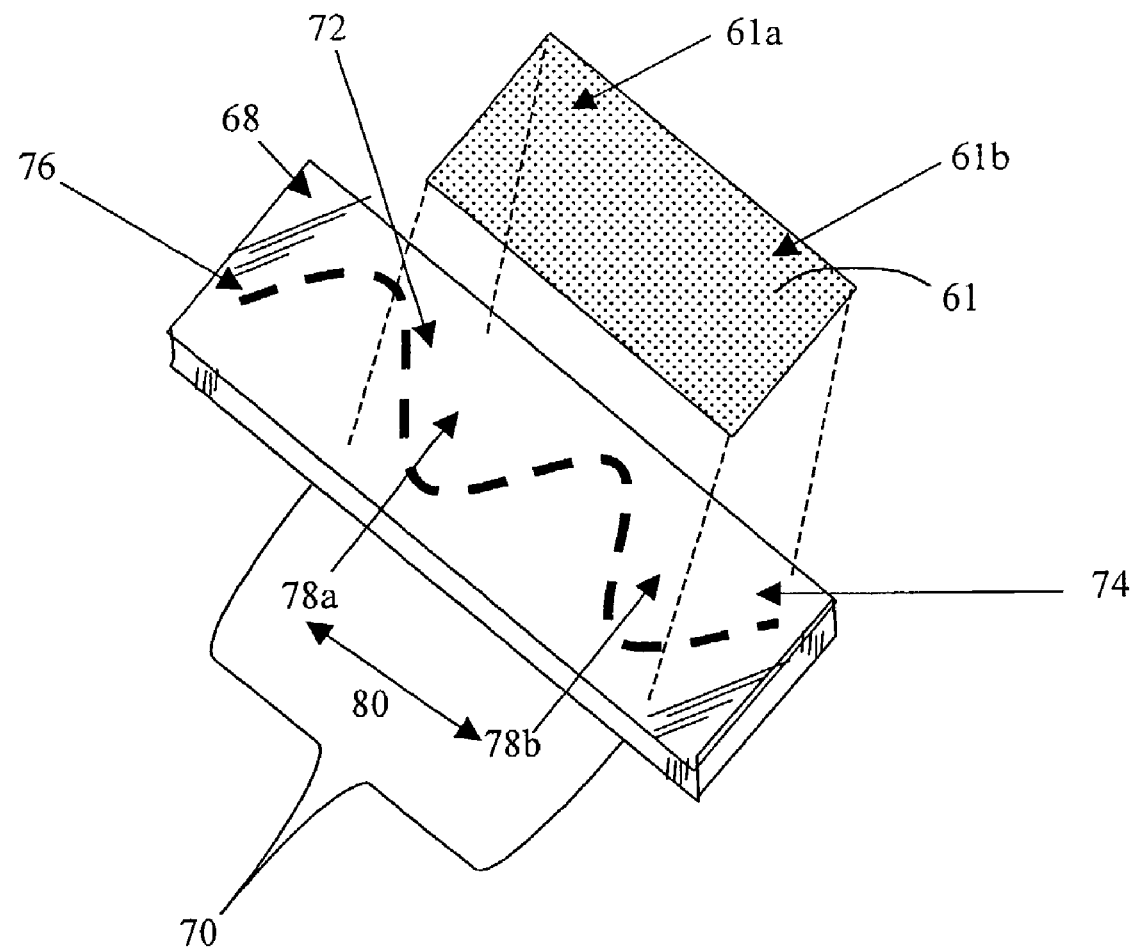
FIG. 6c is a perspective view of the filter shown in FIGS. 6a and 6b and a perspective view of a microscope slide on which the material collected by the filter is to be deposited.

The filter 61 is then removed from the support structure 62 and is positioned over a slide 68, with material oriented to face slide 68 as shown in FIG. 6*c*. Pressure can be applied to the reverse side of filter 61 to assist in transferring the material or cells on the filter 61 to the slide 68. A concentration gradient remains in the deposit area 70. The material or cells at the first end 72 of the deposit area 70 of slide 68 which received the first end 61*a* of the filter 61 will be less concentrated than the material or cells deposited at the second end 74 of the deposit area 70. Because a range of concentrations is provided on a single slide, the concentration gradient can be scanned in various ways to determine an optimal analysis region. For example, scanning could proceed along a path 76 to locate a material concentration which is deemed sufficient for analysis, thus defining a minimal concentration level 78*a*. Human or machine vision scanning proceeds along pathway 76 until a maximum acceptable concentration 78*b* is located. The region between the acceptable minimum concentration level 78*a* and the acceptable maximum concentration level 78*b* is defined as the optimal analysis region 80. The material presented as a concentration gradient, ensures that a region of optimal material concentration will be present on the slide for examination. Artisans in machine vision will also appreciate that for efficiency reasons once an optimal starting point is found, image acquisition may begin and proceed in either direction until that is no longer the case.

When the filter assembly 60 is angled within the sample chamber 64, the sample chamber 64 presents an elliptical internal profile to the round filter assembly 60 and hence may no longer seal around its perimeter in a fluid tight manner. This can be addressed in a number of ways. For use with small angles (up to 30 degrees) the sample chamber 64 is preferably made of elastic material such as rubber and the sample chamber 64 should have an internal diameter that is less than that of the filter assembly 60. Under these conditions, when the filter assembly 60 is positioned horizontally the sample chamber 64 is stretched the most. At increasing angles this deformation decreases until a round filter assembly is no longer held around its circumference by a fluid tight seal. Alternatively, for a given angle, such as 30 degrees, it may be desirable to utilize an elliptical shaped filter assembly instead of a round filter assembly to extend the useful range. In some cases, for example, when preparing many samples in the same manner, a rigid sample chamber with a bonded filter assembly, set a fixed angle, may be desirable. While a wide range of materials and gradients can be achieved using the present invention, artisans will recognize that the depth of the fluid sample introduced into the sample chamber above the filter assembly, the length of the porous filter area and the angle that the filter assembly is held at within the sample chamber are primary contributors to creation of the density gradient.

Figure 7:
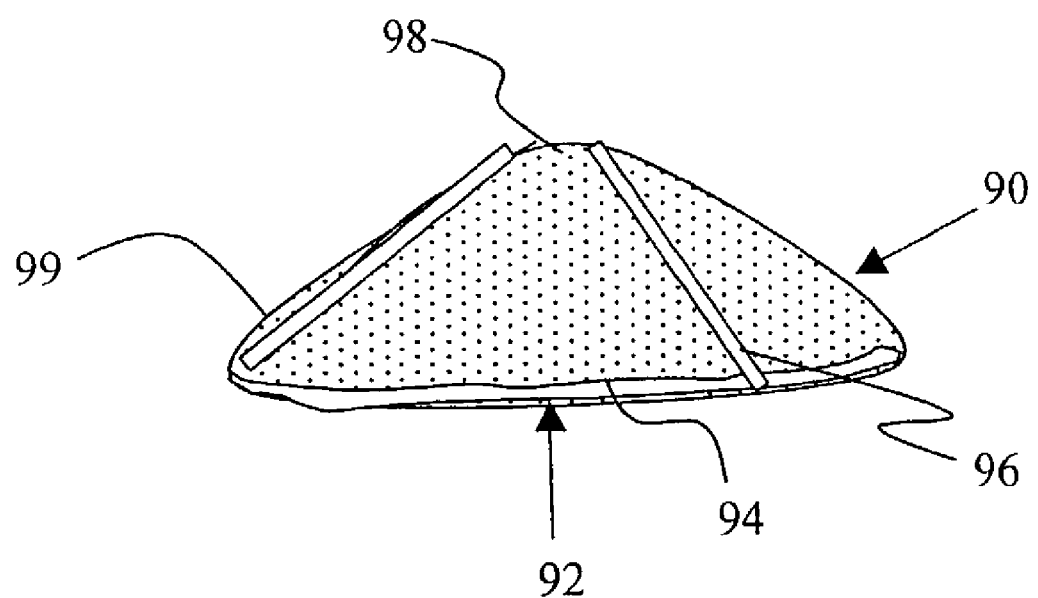
FIG. 7 is a perspective view of yet another embodiment of the present invention.

FIG. 7 shows an alternative embodiment of the present invention. The filter 90 shown in FIG. 7 can be used in manner similar to the filter shown in FIGS. 6*a*, 6*b* and 6*c*. The filter 90 is generally dome shaped and is supported by a structure 92. The support structure 92 includes a generally circular member 94 and arms 96 which extend radially inward from the circular member 94. The arms 94 are also angled upwardly to create a peak region 98. When the sample solution is introduced to the sample chamber a higher volume of the sample solution passes through the filter in the lower portion of the filter 99 than in the peak region 98 of the filter 90. As more of the sample solution passes through the lower portion 99 of the filter 90 than through the peak region 98, a higher concentration of material will be collected at the lower portion 99 of the filter 90 than at the peak region 98. After passing the sample solution through the filter 90, the filter 90 and support structure 92 are removed from the sample chamber. The filter 90 is then removed from the support structure 92. Similar to the process described with respect to FIGS. 6*a*, 6*b*, and 6*c* the material from the filter 90 is then transferred to a slide to create a concentration gradient.

Unlike the filter shown in FIGS. 6*a* and 6*b*, the cone shaped filter 90 can collect a concentration gradient without the need to position the filter 90 at an angle within the sample chamber. However, if desired, the cone-shaped filter can be mounted at an angle to create an even greater variation in concentrations of material on the filter 90. Similarly, an inverted cone or other filter shape may be used to capture and deposit material in a desired gradient.

Additionally, if multiple slides are desired, the filter 90 can be placed over multiple slides, such as for example, as shown in FIG. 2. Alternatively, the filter 90 could be separated into portions (using perforation or by cutting) and each portion of the filter 90 could be used to transfer material on to a slide to create multiple slides with multiple concentration gradients. In this case, separating the filter 90 into uniformly shaped portions will result in concentration gradients with similar characteristics.

Figure 8A:
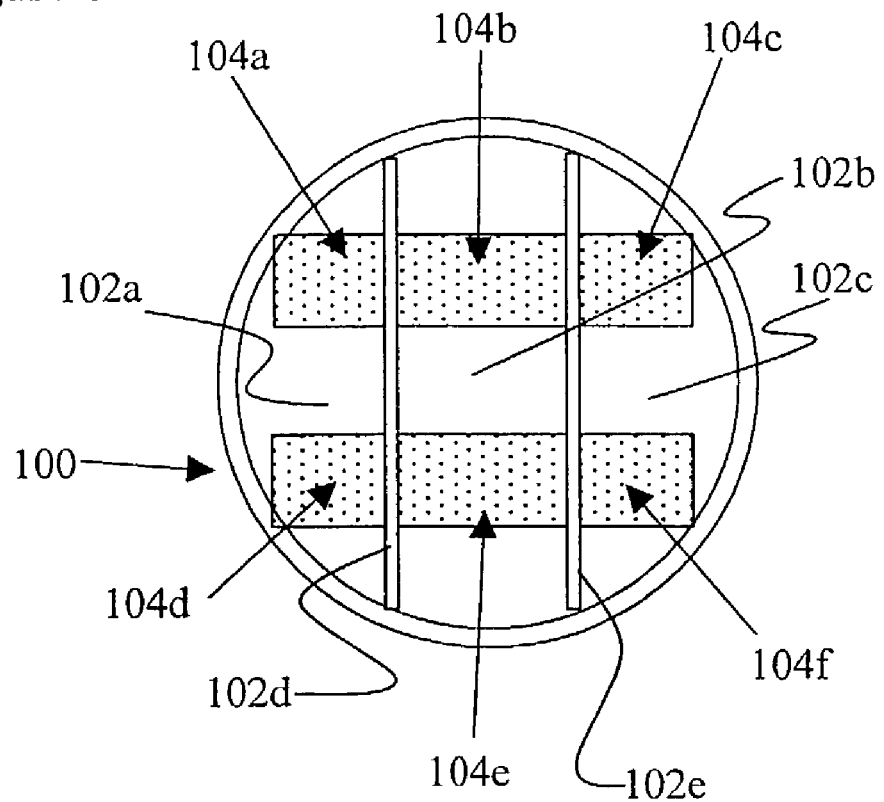
FIG. 8a is a top view of the another embodiment of the present invention.
Figure 8B:
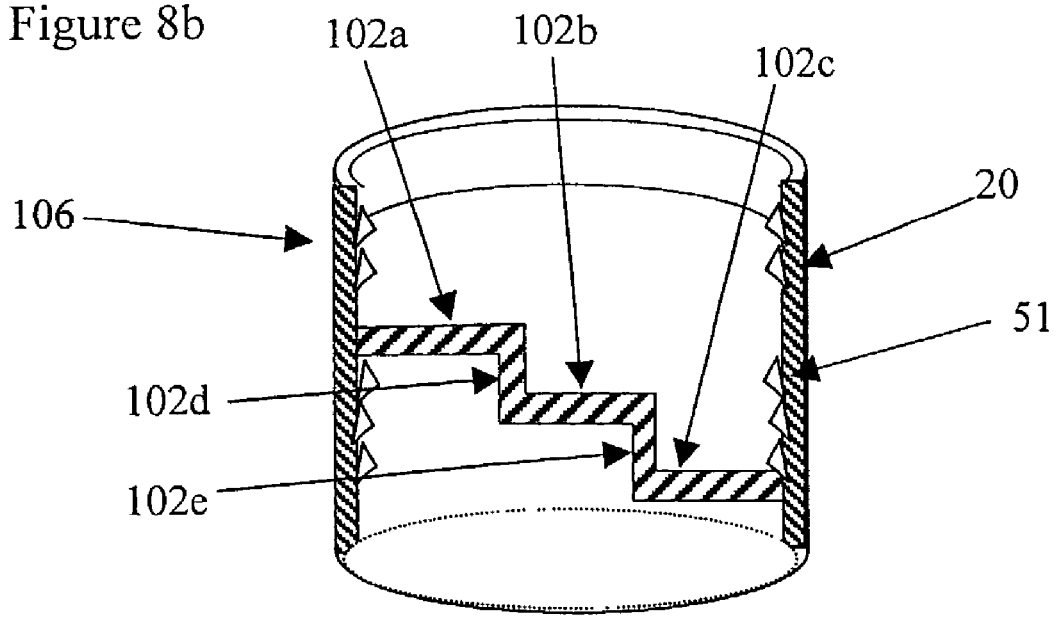
FIG. 8b is a front view of the filter assembly shown in FIG. 8a mounted in a sample chamber.

FIGS. 8*a* and 8*b* show a step-shaped filter assembly 100 for material capture and deposition. The filter assembly 100 includes a support structure 102 and a filter 104. The support structure 102 includes three horizontal stepped levels 102*a*, 102*b*, 102*c*, and two vertical portions 102*d* and 102*e*. As shown in FIG. 8*b*, horizontal portion 102*a* is joined with horizontal portion 102*b* by vertical portion 102*d* and horizontal portion 102*b* is joined with horizontal portion 102*c* by vertical portion 102*e*. The filter 104 includes several portions 104*a*, 104*b*, 104*c*, 104*d*, 104*e*, and 104*f*. Portions 104*a* and 104*d* are mounted to horizontal portion 102*a*, portions 104*b* and 104*e* are mounted to horizontal portion 102*b*, and portions 104*c* and 104*f* are mounted to horizontal portion 102*c*. Alternatively, a single piece filter could be provided which is not portioned. The single piece filter would be mounted to horizontal surface 102*a*, 102*b* and 102*c*. In addition the single piece filter would overlie vertical portions 102*d*, 102*e*. Although the sample suspension would not pass through portions of the filter which overlie vertical portions 102*d* and 102*e*, such a filter would provide acceptable results for some applications.

When placed within the sample chamber 106, the support structure 102 provides a fluid tight seal between the interior surface of the sample chamber 106 and the support structure 102. Protrusions 108 extend from the interior surface of the sample chamber 106 and provide a variety of locations at which the support structure 102 can be positioned.

When sample suspension is introduced from above the support structure 102 and filter 104, material is captured by the filter 104. Again, vacuum may be used to facilitate the passage of fluid through the filter 104 and capture of material by the filter 104. Because a smaller volume of sample solution will flow through portions 104*a* and 104*d* than through portions 104*b* and 104*e*, the concentration of material collected on filter portions 104*b* and 104*e* will be greater than the concentration of material collected on filter portions 104*a* and 104*d*. Likewise, because a smaller volume of sample solution will flow through portions 104*b* and 104*e* than through portions 104c and 104f, the concentration of material collected on filter portions 104c and 104f will be greater than the concentration of material collected on filter portions 104b and 104e.

When the filter 104 is removed from the sample chamber 106, the filter portions can be used to create slides with varying concentrations of deposited material. These varying concentrations of deposited material can be useful for diagnostic techniques based on malignancy-associated changes or other biological methods. The invention provides the varying concentrations of deposited materials without the need for preparing several dilutions of the sample fluid.

Figure 9A:
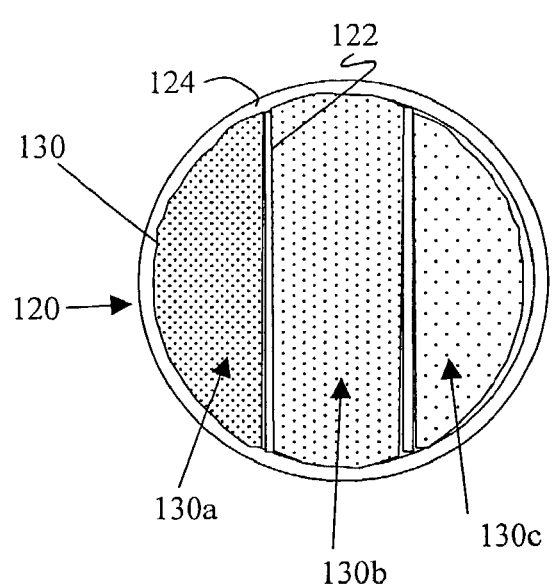
FIG. 9a is a top view of another embodiment of the present invention.
Figure 9B:
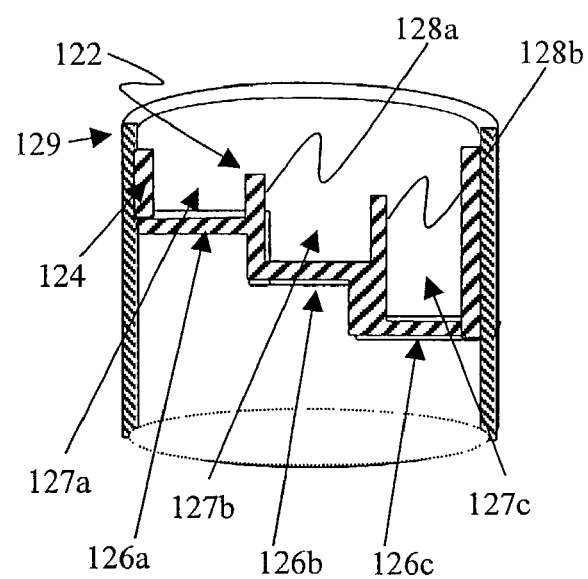
FIG. 9b is a front view of the filter assembly shown in FIG. 9a mounted in a sample chamber.

FIGS. 9a and 9b shows another embodiment of the present invention. The filter assembly 120 includes the support structure 122 and filter 130. The support structure 122 includes a circular rising outer wall 124, three horizontal portions 126a, 126b, and 126c, and two vertical portions 128a and 128b. The filter 130 includes portions 130a, 130b, and 130c. Filter portion 130a is a "fine" grade filter which allows for the passage of very small particles, filter portion 130b is a "medium" grade filter which allows for the passage of medium sized particles, and filter portion 130c is a "course" grade filter which allows for the passage of larger sized particles.

In this configuration, sample suspension may be introduced into the individual sub-chambers 127a, 127b, 127c, formed between the outer chamber walls of the support structure 124 and its inner supporting partitions 128a, 128b. However, this floodgate, or weir, design supports another method. Sample suspension may be introduced into sub-chamber 127a until full. The design is such that rising structure of the support 122, designated as 128a, is lower than the surrounding chamber walls formed by support structure 124. Therefore, substantially all of the overflow from sub-chamber 127a flows into sub-chamber 127b. Similarly, after sub-chamber 127b is full, additional sample suspension overflows from sub-chamber 127b into sub-chamber 127c.

Such a configuration may be useful for preferentially capturing various sample components. In the case of gynecological samples, for example, the smallest pores could capture viruses such as HPV, the middle layer could capture material such as epithelial cells, and the coarse area could capture cell clumps. Similarly, for lung-related tests, viral capture could facilitate a TB test while other material could be used for other assays such as cancer detection, for example.

It should also be clear that the filter portions 130a, 130b, etc., could be angled or otherwise arranged so as to capture material as a density gradient, at the same time. It should also be clear that the filters of FIGS. 8a, 8b, 9a, and 9b can be designed in radial or other manners to achieve the same effects.

While preferred embodiments of the present invention are shown and described, it is envisioned that those skilled in the art may devise various modifications of the present invention without departing from the spirit and scope of the appended claims.

We claim:

1. An apparatus comprising:
   a sample chamber for holding a sample suspension, said chamber comprising an opening for receiving a sample suspension, an outer wall, and a filter support comprising a first step having a first depth from said opening, a second step having a second depth from said opening that is greater than said first depth, and a third step having a third depth from said opening that is greater than said second depth;
   a first vertical weir extending a first distance from said first step of said filter support, said first vertical weir, said outer wall, and said first step defining a first sub-chamber; a second vertical weir extending a second distance from said second step of said filter support, said second distance being less than said first distance, said first vertical weir, said second vertical weir, said outer wall, and said second step defining a second sub-chamber, and said second vertical weir, said outer wall, and said third step defining a third sub-chamber; and
   means for drawing the sample suspension through a filter mounted on said filter support.

2. The apparatus of claim 1, wherein said filter comprises a plurality of portions, a first one of said plurality of portions mounted on said first step, a second one of said plurality of portions mounted on said second step, and a third one of said plurality of portions mounted on said third step.

3. The apparatus of claim 2, wherein at least one of said plurality of portions has a first porosity and at least one of said plurality of portions has a second porosity.

* * * * *